United States Patent
Baker et al.

[11] Patent Number: 6,079,285
[45] Date of Patent: Jun. 27, 2000

[54] ROBOTIC SAMPLER FOR REMOTE SAMPLING OF LIQUIDS IN A PROCESS STREAM

[76] Inventors: Jack T. Baker, P.O. Box 116, Greenwich, N.Y. 12834-0116; Myles Miller, 51 Walnut St., Glens Falls, N.Y. 12801

[21] Appl. No.: 09/313,621

[22] Filed: May 18, 1999

Related U.S. Application Data

[63] Continuation of application No. 08/942,086, Oct. 1, 1997, abandoned.

[51] Int. Cl.[7] .................................................. G01N 1/00
[52] U.S. Cl. ............................................................ 73/865.8
[58] Field of Search ............... 73/865.8, 863.81–863.85, 73/864.34, 864.35, 864.73, 864.44, 864.45

[56] References Cited

U.S. PATENT DOCUMENTS

| | | | |
|---|---|---|---|
| 2,679,435 | 5/1954 | Finan | 301/45 |
| 2,781,813 | 2/1957 | Ferguson | 152/208 |
| 2,841,199 | 7/1958 | Voelkel et al. | 152/208 |
| 3,239,277 | 3/1966 | Beck | 301/47 |
| 4,003,261 | 1/1977 | Nautet et al. | 73/423 R |
| 4,169,758 | 10/1979 | Blackstone et al. | 176/19 R |
| 4,475,410 | 10/1984 | Jaeger | 73/863.84 |
| 4,483,205 | 11/1984 | Bellaiche et al. | 73/863.23 |
| 4,601,519 | 7/1986 | D'Andrade | 301/45 |
| 4,676,289 | 6/1987 | Yi Su | 152/210 |
| 4,709,265 | 11/1987 | Silverman et al. | 358/108 |
| 4,815,513 | 3/1989 | Hirakawa | 153/210 |
| 5,117,897 | 6/1992 | Robert | 165/11.2 |
| 5,146,796 | 9/1992 | Mailliet et al. | 73/863.82 |
| 5,203,646 | 4/1993 | Landsberger et al. | 405/191 |
| 5,296,197 | 3/1994 | Newberg et al. | 73/863.82 |
| 5,350,033 | 9/1994 | Kraft | 180/167 |
| 5,408,883 | 4/1995 | Clark, Jr. et al. | 73/601 |
| 5,411,070 | 5/1995 | Yadegar | 152/210 |
| 5,423,230 | 6/1995 | Olander et al. | 73/865.8 |

FOREIGN PATENT DOCUMENTS

| | | | |
|---|---|---|---|
| 004318164 | 12/1993 | Germany | 73/865.8 |

*Primary Examiner*—Robert Raevis
*Attorney, Agent, or Firm*—Seidel, Gonda, Lavorgna & Monaco, PC

[57] ABSTRACT

A robotic sampling device has a maneuverable, telescoping sample collector comprising a sample collecting arm and a propulsion module containing means for supporting and facilitating movement. Most preferably, the means for supporting and facilitating movement are wheels. The robotic sampling device also contains means for increasing traction for the propulsion module. The sampling device is remotely controlled. The sampling device contains at least one light source and a viewer that provides information for navigation and sample collection. The wheels of the propulsion module contain extendable pins which promote increased traction. The telescoping sample collector may also be rotated or tilted through a 180 degree arc relative to the axis of the pipe. The robotic sampling device also provides a means for collecting, labelling, and storing a sample, as well as cleaning the sample collector in preparation of another sampling event.

28 Claims, 8 Drawing Sheets

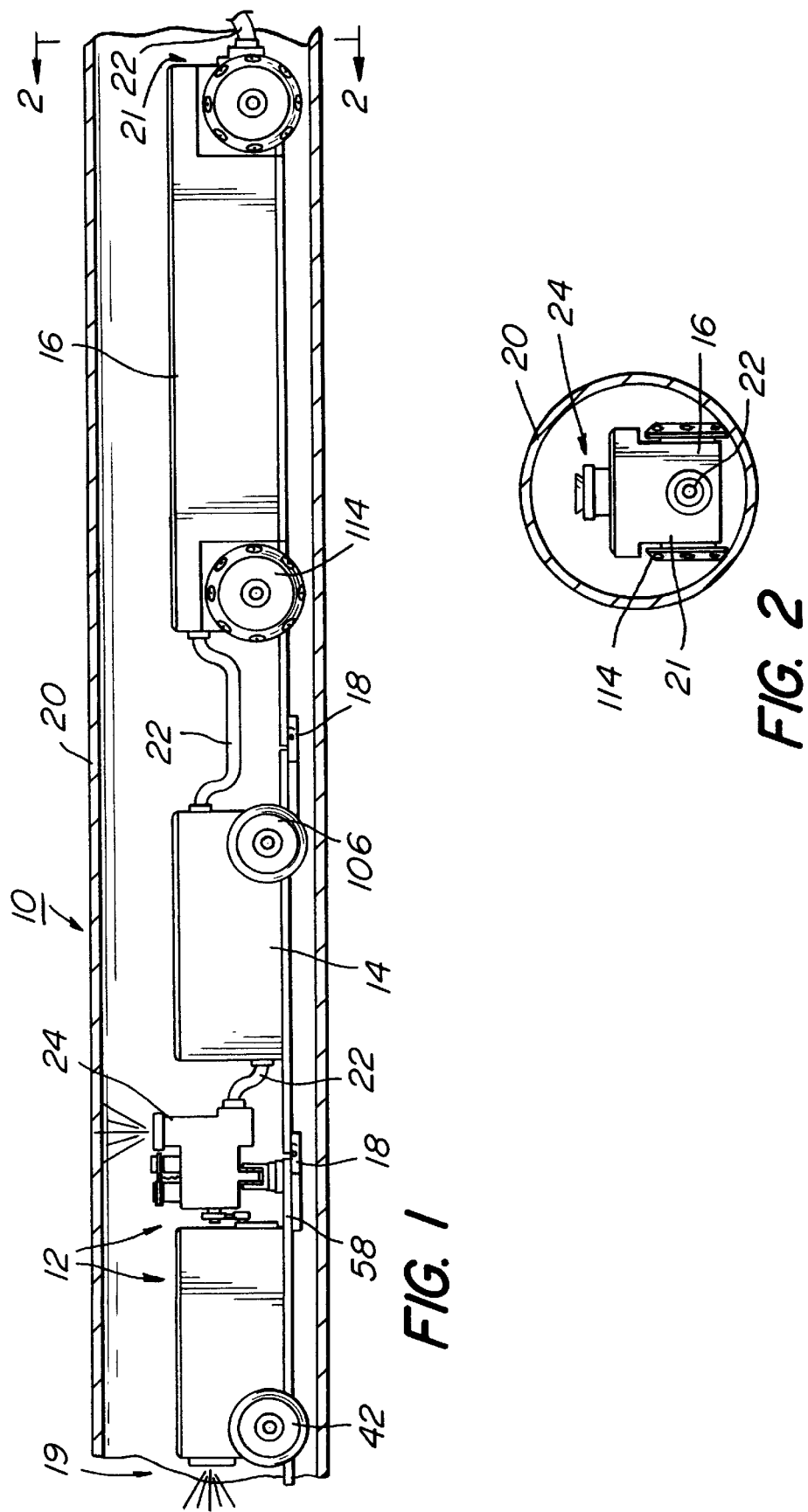

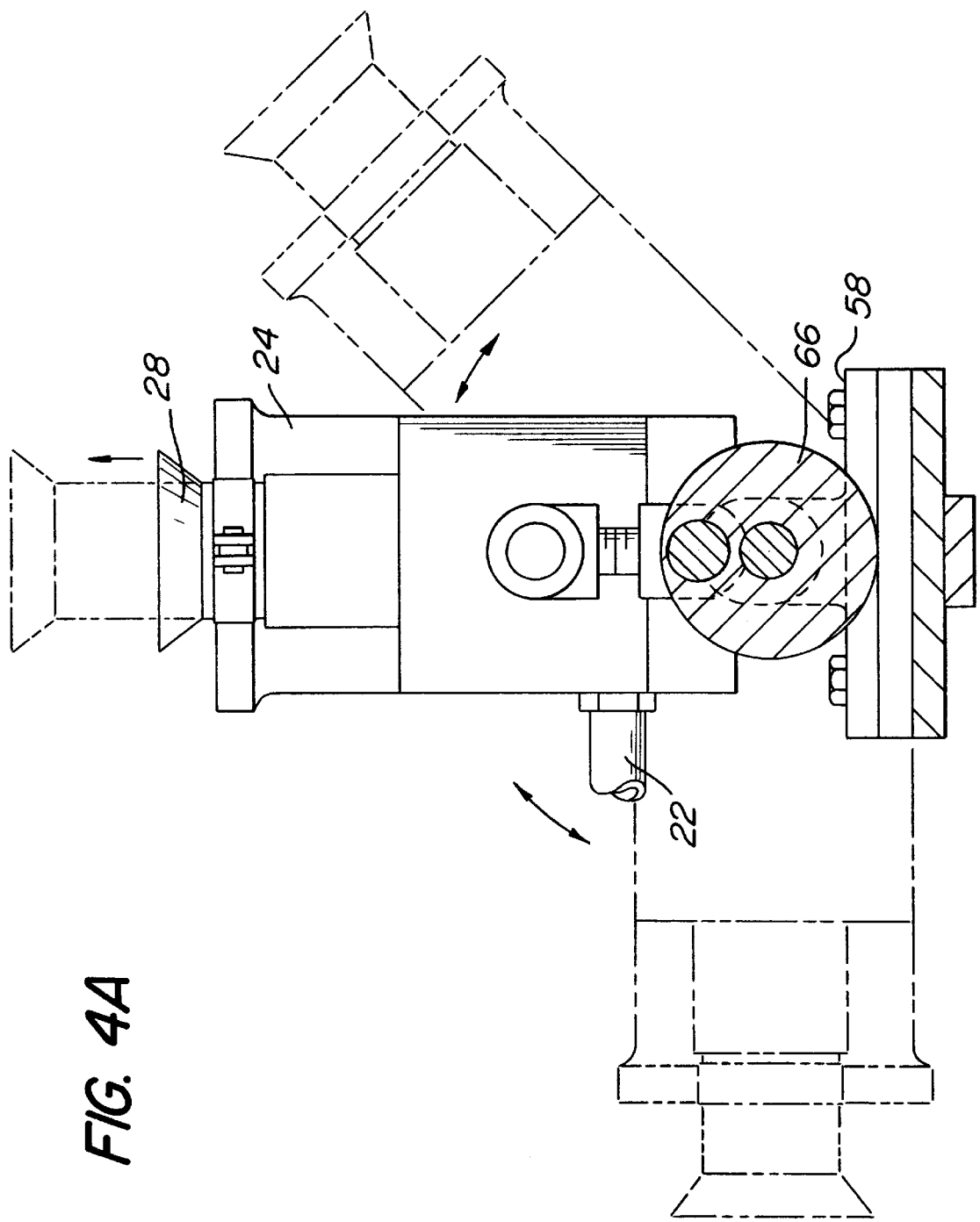

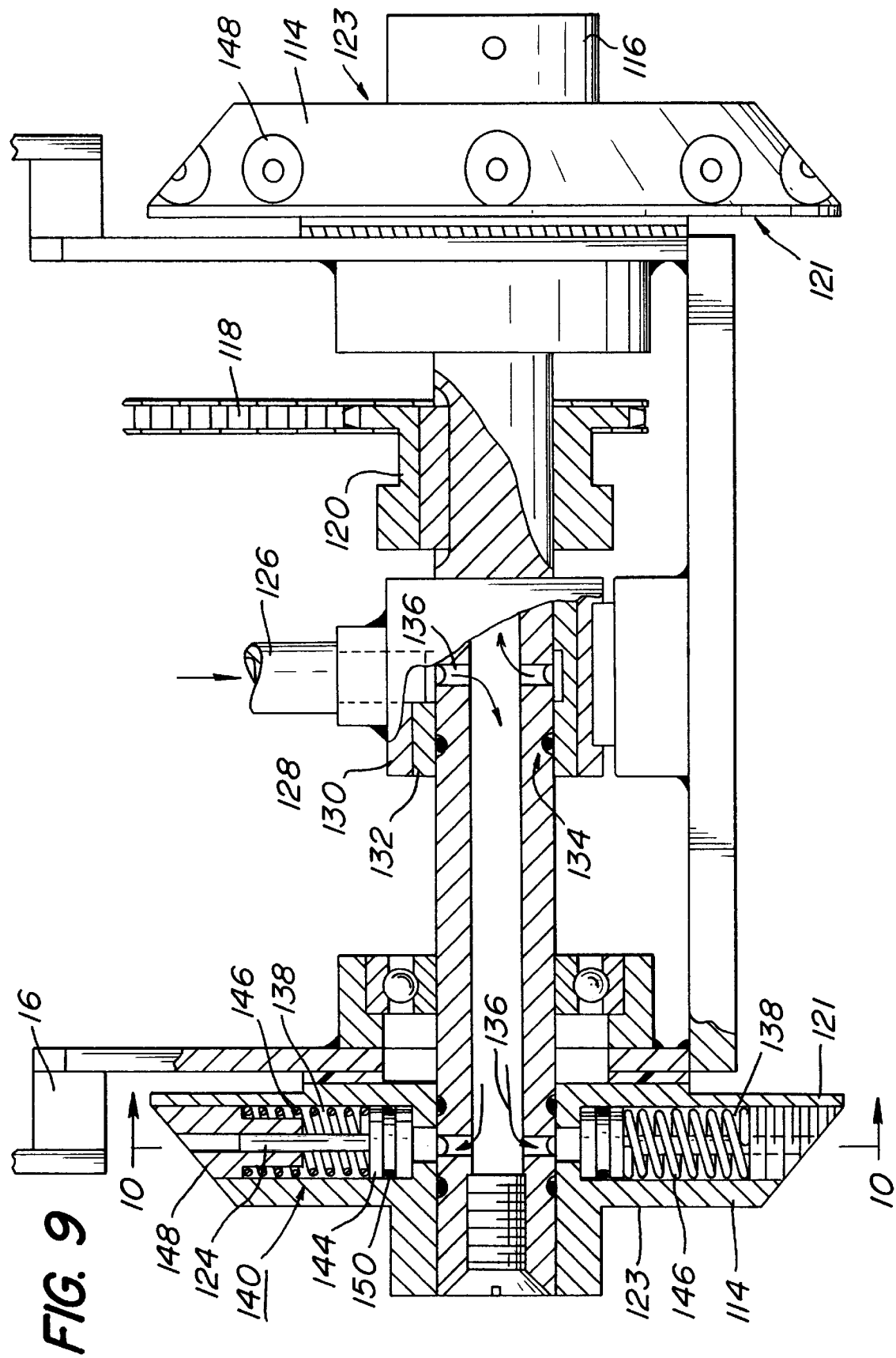

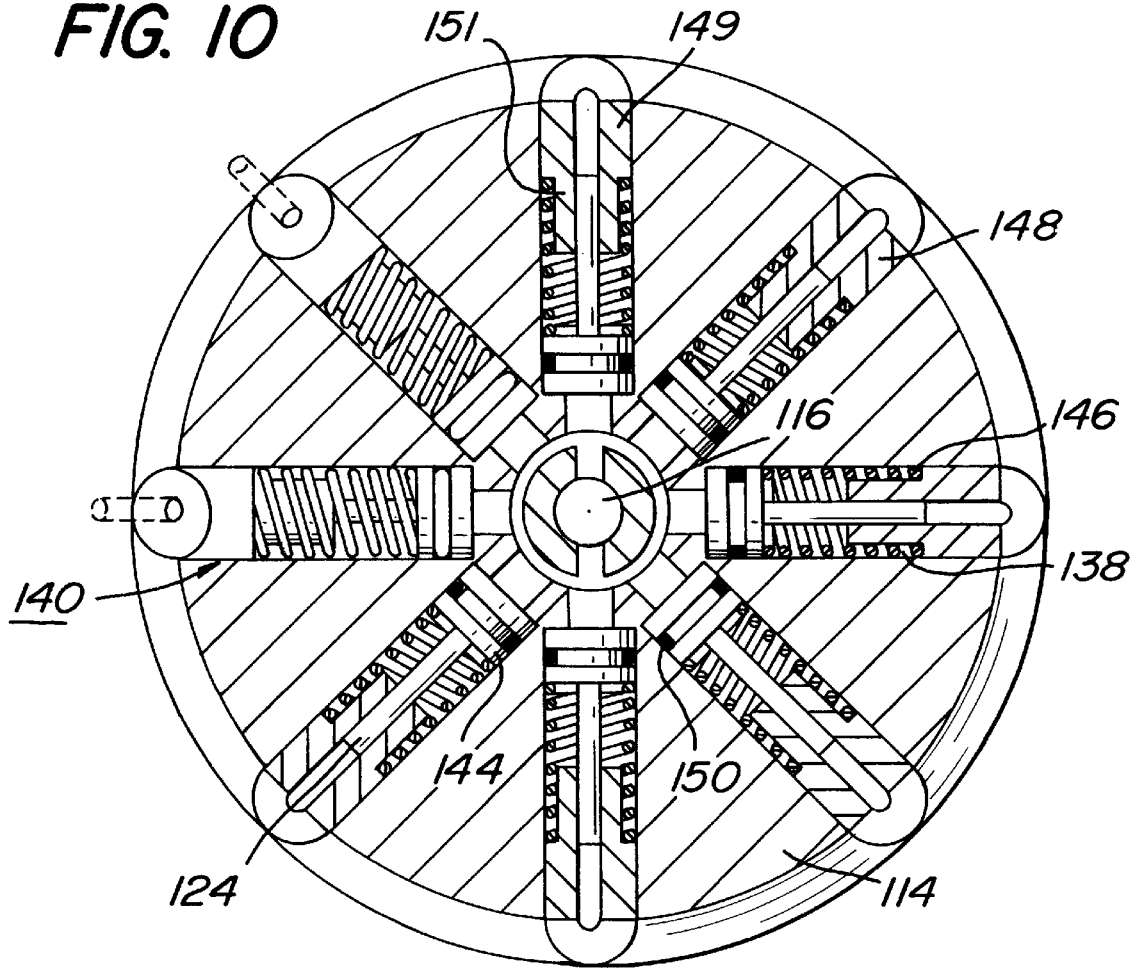

ROBOTIC SAMPLER FOR REMOTE SAMPLING OF LIQUIDS IN A PROCESS STREAM

This is a continuation of application Ser. No. 08/942,086 filed on Oct. 1, 1997, now abandoned.

FIELD OF THE INVENTION

This invention relates generally to remotely operated, robotic sampling devices, and specifically to a robotic sampling unit that can collect multiple samples in a process stream within the confines of a piping network.

BACKGROUND OF THE INVENTION

It is necessary to sample the contents of fluid streams delivered through piping networks, such as wastewater within underground pipe. Environmental laws and regulations often require the reporting of sampled concentrations of specific substances in wastewater streams for compliance purposes. Such fluid streams are usually rich in particulates or contaminating matter. Permanent, in-line sampling devices, such as those including sampling ports, are easily disabled because they can become clogged. Permanently established sampling ports may also suffer the corrosive effects, over time, of the fluid stream's constituents. Such sampling devices are also difficult to clean, thus increasing experimental error. Permanent sampling ports may also be impractical if the piping diameter is too large or the piping inaccessible. It may also be desirable, for safety reasons, that human beings not be exposed to the sampled product, which would rule out manual sample collection.

However, sampling at specific locations, such as that provided by the sampling ports, may nonetheless be desired. For example, in a piping network in which several tributary lines join one main line, the performance of a process may best be measured by sampling the various tributary lines at the point they open to the main, before the two streams become mixed. In contrast, though, randomly chosen sampling locations may also be desired. In complicated piping networks, areas of inefficiencies or possible design failures can sometimes be detected by sampling the concentrations of the process stream therein. These areas, or "hot-spots," readily change location as the prevailing process stream conditions change, making fixed sampling ports useless.

Robotic sampling devices offer a solution to the problem of obtaining samples in underground piping networks. These devices can be remotely operated and samples taken from specific areas as long as the robotic device can reach those specific locations.

Several engineering problems, however, accompany the use of robotic devices. The devices must be operable in submerged or nearly-submerged conditions. The devices must be able to traverse a variety of terrains within the interior of the piping network containing sedimentation, sludge, and the like. The device must be able to collect a sample from specific but varied locations relative to the device. The device should also be able to store a collected sample, label or identify the sample, automatically clean its sample collection system, and prepare the collection system for another sampling event.

SUMMARY OF THE INVENTION

A robotic sampling device for collecting samples from process streams in piping networks has been developed that overcomes these engineering problems. The robotic sampling device of the present invention has a maneuverable, telescoping sample collector comprising a sample collecting arm and a propulsion module containing means for supporting and facilitating movement. Most preferably, the means for supporting and facilitating movement are wheels. The robotic sampling device also contains means for increasing traction for the propulsion module. The invention is remotely controlled. The sampling device contains at least one light source and a viewer that provides information for navigation and sample collection.

In the preferred embodiment of the invention, the wheels of the propulsion module contain extendable pins which promote increased traction. The telescoping sample collector may also be rotated or tilted through a 180 degree arc relative to the axis of the pipe. The robotic sampling device also provides a means for collecting, labelling, and storing a sample, as well as cleaning the sample collector in preparation of another sampling event.

BRIEF DESCRIPTION OF THE DRAWINGS

FIG. 1 is an elevational view of a robotic sampling device of the present invention.

FIG. 2 is a sectional view taken along line 2—2 of FIG. 1.

FIG. 4a is the enlarged sectional view of FIG. 4, particularly showing, in phantom, the variety of positions the telescopic housing may be tilted, as well as the extension of the telescopic sampling arm.

FIG. 9 is an enlarged cross-sectional view taken along line 9—9 of FIG. 8, particularly showing a drive shaft and traction wheel.

FIG. 10 is a cross-sectional view taken along line 10—10 of FIG. 9, particularly showing a traction wheel.

DETAILED DESCRIPTION OF THE INVENTION

Figure 3:
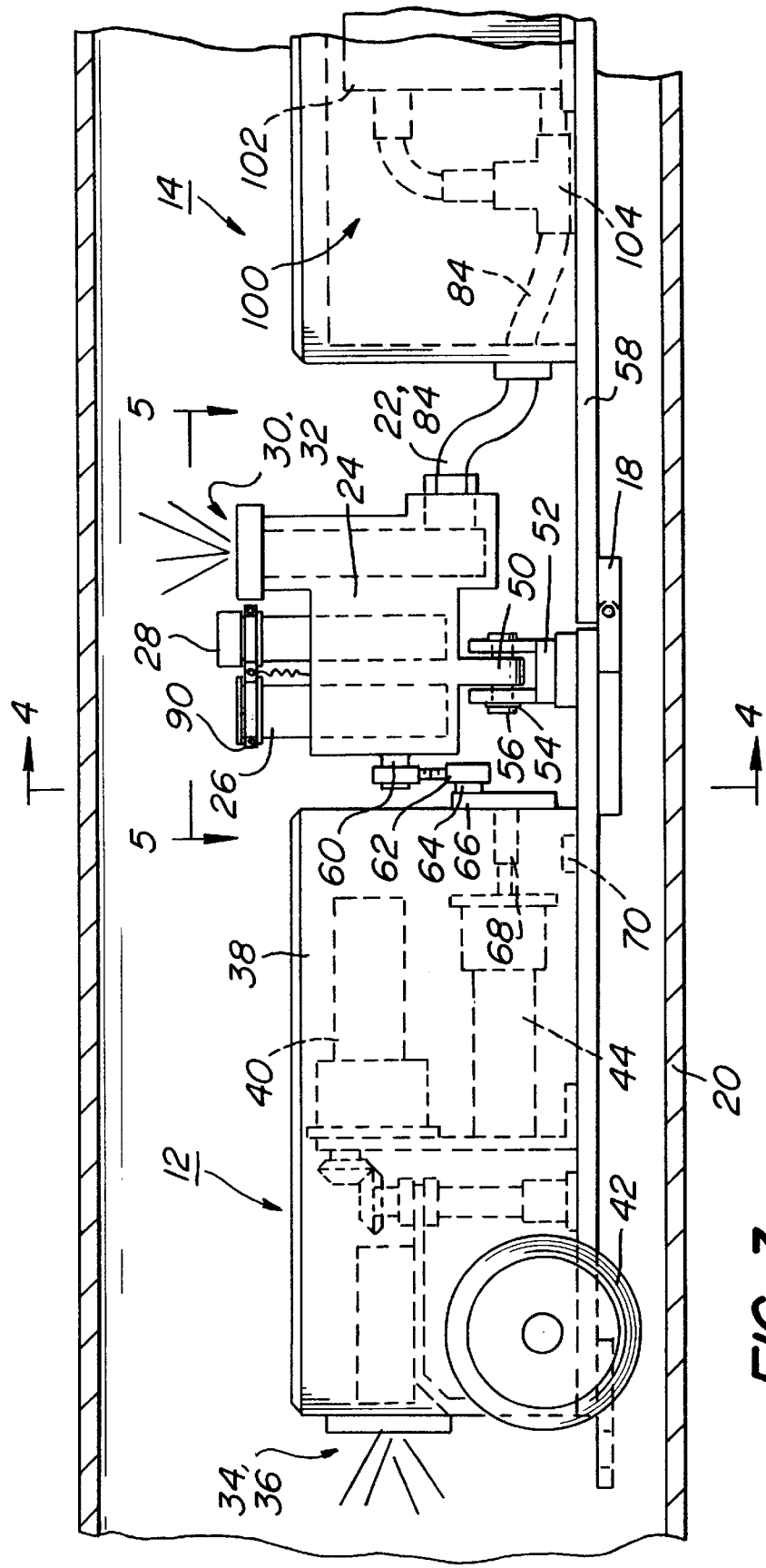
FIG. 3 is an enlarged elevational view of the robotic sampling device of FIG. 1, particularly showing a sample collecting module and the pumping module of the present invention.
Figure 4:
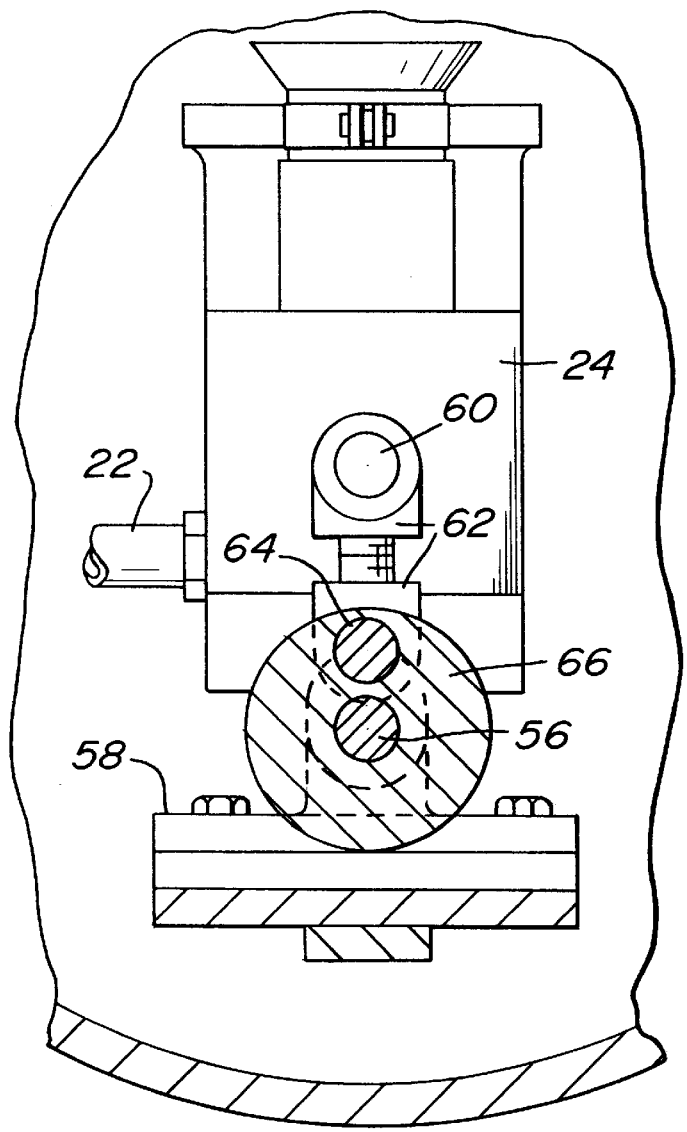
FIG. 4 is an enlarged sectional view taken along line 4—4 of FIG. 3, particularly showing a telescopic module's rotating mechanism.

The robotic sampling device of the present invention is shown in FIG. 1, generally referred to by the numeral 10. The robotic sampling device 10 generally comprises three modules: a sample collecting module 12, a pump module 14, and a propulsion module 16. The three modules are joined in a linear fashion by couplings 18 to form an operational unit having a front end 19 and a back end 21. The robotic sampling unit 10 is designed to move through piping 20. In the preferred embodiment of the invention, the dimensions of the robotic sampler 10 are chosen so that the robotic sampler may operate in pipe having an eight inch diameter and greater. It is contemplated that the size of the robotic sampling unit 10 will be determined by the piping size group, such one size for 8–18 inch pipe and another size for 20–30 inch pipe, and so forth. The robotic sampling unit 10 may move in forward and reverse directions, and may also be adapted to be pulled through the pipe 20. More particularly, the robotic sampling unit 10 may sample liquids in a process stream, such as wastewater in an underground piping system. The robotic sampling unit 10 is completely waterproof and operational in a submerged state.

The robotic sampler 10 is remotely operated. An umbilical cord 22 connects the various modules comprising the robotic sampler 10 to a central command console (not shown in the drawings). A rewinder unit (not shown in the drawings) feeds the umbilical cord 22 as the robotic sampler 10 mobilizes in the pipe 20. The rewinder determines the distance the robotic sampler 10 travels within the pipe from the length of umbilical cord 22 utilized and that information is displayed and recorded by the command console. The umbilical cord 22 contains a plurality of independent lines each supplying specific parts of the robotic sampler 10 with either electrical power or compressed air. These independent lines each have a smaller diameter than the umbilical cord 22. A technician, or operator, can control the movement of the robotic sampler 10, as well as the sampling system, by closing electric switches. Certain functions of the robotic sampler 10, as described in more detail below, are enabled by a supply of compressed air through the umbilical cord 22. The robotic sampler 10 may also accommodate 12 volt or 24 volt batteries.

The sample collecting module 12 is shown in FIG. 3. A telescopic housing 24 houses an air piston 26, a suction intake (sampling) telescope 28, and, as better shown in FIG. 5, a camera 30 and a light source 32. The camera 30 and light source 32 permit the operator to view the sample area. The camera 30 and the light source 32 are powered by electricity supplied by the umbilical cord 22. The camera 30 relays a video image to the operator who may view the image on a TV screen. The camera 30 and light source 32 are preferably located on the sample collecting module 12 next to the telescopic sampler 28 so that the operator may accurately view the area to be sampled. A front camera 34 and a front light 36 are also located on the front end 19 of the robotic sampler 10. The front camera 34 and the front light 36 enable the operator to view the interior of the pipe 20 as the robotic sampler 10 moves forward. The front camera 34 may be articulated in a variety of directions by a motor 40. The operator remotely controls the position of the front camera 34. The robotic sampler 10 of the present invention is not limited to video cameras as a means for viewing the navigable area and sampling area; fiber optic or sonar devices are also contemplated. The sample collecting module 12 contains at least one set of wheels 42, preferably located at the front of the sample collecting module 12. The pump module 14 also contains at least one set of wheels 106.

The telescopic sampler 28 may be extended into and retracted from a sampling stream. The extension or retraction of the sampling telescope 28 is controlled by the air piston 26. The maneuverable telescopic housing 24 can be rotated, or tilted, through a 180 degree arc (relative to the axis of the pipe 20 in which the locator unit is operating). The telescopic housing 24 is not designed to tilt forward or backward. A motor 44 is employed to move the telescopic housing 24 to the desired angular position. The operator may then maneuver the telescopic sampler 28 into a liquid stream by controlling its extension. In a preferred embodiment for pipe having a diameter from about 8 inches to about 18 inches, the telescopic sampler 28 may be extended about 3.7 inches. The extension of the telescopic sampler 28 is not necessarily limited by the interior diameter of the pipe, for it is preferable that the telescopic sampler 28 be able to reach into adjoining tributary pipes.

FIGS. 4 through 7 more clearly illustrate the telescopic housing 24. A mounting shaft 50 is coupled to a mounting bracket 52 with a washer 54 and pin 56. The mounting bracket 52 is secured to a platform 58. As shown in FIG. 4a, this assembly permits the telescopic housing 24 to rotate, or tilt, along a 180 degree arc, relative to the pipe 20. The mounting shaft 50 is centrally located on the underside of the telescopic housing 24. The rotation of the telescopic housing 24 is actuated by the motor 44. The motor 44 is located in the motor housing 38, which in turn is positioned on the platform 58. A shaft 60 on the telescopic housing 24 is attached to a connecting rod 62. The connecting rod 62 is connected and keyed to a coupling 64 and a mounting bracket 66. The mounting bracket 66 is connected to the motor 44 via a drive shaft 68. The motor 44 is remotely and electronically controlled. A tilt switch 70 is located in the motor housing 38. The tilt switch 70 stops the robotic sampler 10 if the motor housing 38 tilts beyond a preset angle as it moves through the pipe.

The air piston 26 controls the extension and retraction of the telescopic sampler 28. A cylinder 80 is secured to the telescopic housing 24. In a preferred embodiment of the robotic sampling unit 10, the cylinder 80 is screwed into the telescopic housing 24. The air piston 26 is positioned within the cylinder 80. Both the cylinder 80 and air piston 26 are preferably made of 25% glass-filled teflon. The piston 26 is actuated by compressed air fed to the piston 26 at about 50 psi. The air is supplied through an air line which is part of the umbilical cord 22.

A telescopic sampler casing 82 is secured to the telescopic housing 24. In a preferred embodiment, the telescopic sampler casing 82 is screwed into the telescopic holder 24. The telescopic sampler 28 is positioned within the telescopic sampler casing 82. Both the telescopic sampler casing 82 and the telescopic sampler 28 are preferably made of 25% glass-filled teflon. The telescopic sampler 28 is attached, at its base, to a sample line 84.

A clamp 90 attaches the telescopic sampler 28 to the air piston 26. When the cylinder 80 is pressurized with compressed air, the air piston 26 extends upward, pulling the telescopic sampler 28 with it. The amount of extension is controlled by air pressure acting against an opposing spring 92. The spring 92 has one end attached to the clamp 90 and the other end to the telescopic housing 24. In the embodiment of the invention shown in FIG. 6, the spring 92 is located between the air piston 26 and telescopic sampler 28. The operator can control the extension of the telescope 28 from the control panel by increasing or decreasing air pressure supplied to the cylinder 80.

When the sampling process in complete, the operator closes an air switch (not shown in the drawings). Air then bleeds out of the piston 26 through an orifice 94, allowing the air piston 26 and telescopic sampler 28 to retract under spring tension supplied by spring 92.

When the telescopic sampler 28 is positioned into an incoming flow, the operator may take a sample of the process stream. As shown in FIG. 3, a pump assembly 100 is provided within the pump module 14. The pump assembly 100 is electronically and remotely operated via the umbilical cord 22. The pump assembly 100 allows a sample to be collected through the telescopic sampler 28. The sample line 84 is attached to the pump assembly 100, thus joining the telescopic sampler 28 to the pump assembly 100. As pump 102 draws a measured sample through the telescopic sampler 28 and the sample line 84, the sampled flow, or analyte, is directed to a laboratory container (not shown in the drawings) located at the operator's station by a three-way solenoid valve 104. The pump assembly 100 contains means (not shown in the drawings) for dispensing the analyte to a laboratory container. Once in the laboratory container, the container is sealed, labelled and stored for later analysis. The remote operator, through keyboard control, supplies the information to a labeler (not shown in the drawings) which records a record for each sample taken. A videotape supplied with location information and sample code number may serve as the record. The operator, for example, might include such information as the sample number, time sampled, and location sampled.

Sampling is more specifically carried out as follows. The remote operator may throw a switch automatically controlling the pump assembly 100, drawing a sample when a flow sensor (not shown in the drawings) detects water flow from a tributary pipe. A time may be programmed, for example, to allow sampling in 15 minute increments, or any period required. A sensor at the container filling station detects when the laboratory container is full. A 24 hour supply of sample collection containers may be stored in a magazine. As noted above, a labeler or coder stamps each bottle with relevant sampling information.

The robotic sampler 10 has a flushing system. Distilled water is stored in a container at the operator's station (not shown in the drawings). The operator activates a switch valve (not shown in the drawings) in the solenoid valve 104 that permits the directed backflow of distilled water through the sample line 84 and the telescopic sampler 28. The entire telescopic sampling system is back-flushed with distilled water and readied for another sampling event.

Figure 8:
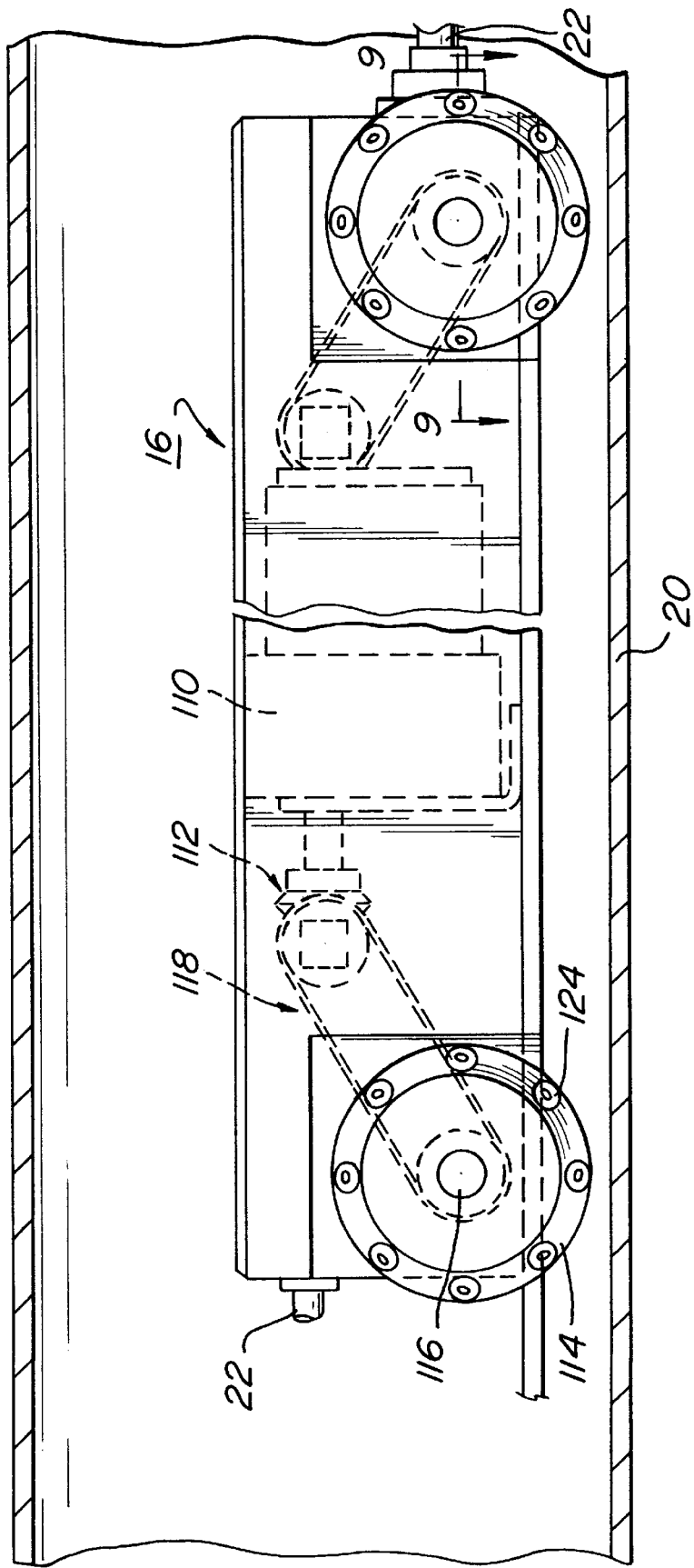
FIG. 8 is an enlarged elevational view of the robotic sampling device of FIG. 1, particularly showing a propulsion module of the present invention.

The propulsion module 16 is shown in FIG. 8. The remotely operated drive module 16 propels the locator sampling unit 10 through the pipes 20. The drive module 16 contains a drive motor 110 and transmission equipment 112 to power the robotic sampling unit 10. The drive module 16 has at least four traction wheels 114, preferably with two traction wheels 114 on each of two drive shafts 116. As better shown in FIG. 10, a chain 118 connects the drive motor 110 to a sprocket 120 on each drive shaft 116. A belt may be utilized instead of the preferred chain 118. The drive module 16 has four-wheel drive. The traction wheels 114 of the drive module 16 are tapered so that the inner diameter 121 of the wheel is larger than the outer diameter of the wheel 123. The tapered traction wheel 114 maximizes the surface of the traction wheel 114 that contacts with the curved surface of a pipe's interior geometry.

Because the robotic sampling unit 10 is expected to encounter traction-reducing sludge, dirt, or sediment while moving along through pipe 20, the traction wheels 114 are equipped with extendable and retractable pins 124. The pins 124 are located at a plurality of locations around the circumference of each of the two wheels 114. Most preferably, eight pins 124 are equally spaced at 45 degree positions along the circular perimeter of the traction wheel 114. The pins 124, when extended, permit increased traction.

The pins 124 may be extended, or activated, by the force of compressed air delivered to the drive shaft 116. An air hose 126 is connected to a half-coupling 128, which is in turn welded to an air header 130. The drive shaft 116 passes through a bushing 132 which is connected to the air header 130. The air hose 126 is positioned along the shaft 116 at a point approximately equidistant from both wheels 114. The drive shaft 116 is machined to receive o-rings 134 at the location of the air header 130 to seal and maintain air pressure. Compressed air passes into the drive shaft 116, and is directed through ports 136 and into the eight cavities 138 housing a pin assembly 140.

Figure 5:
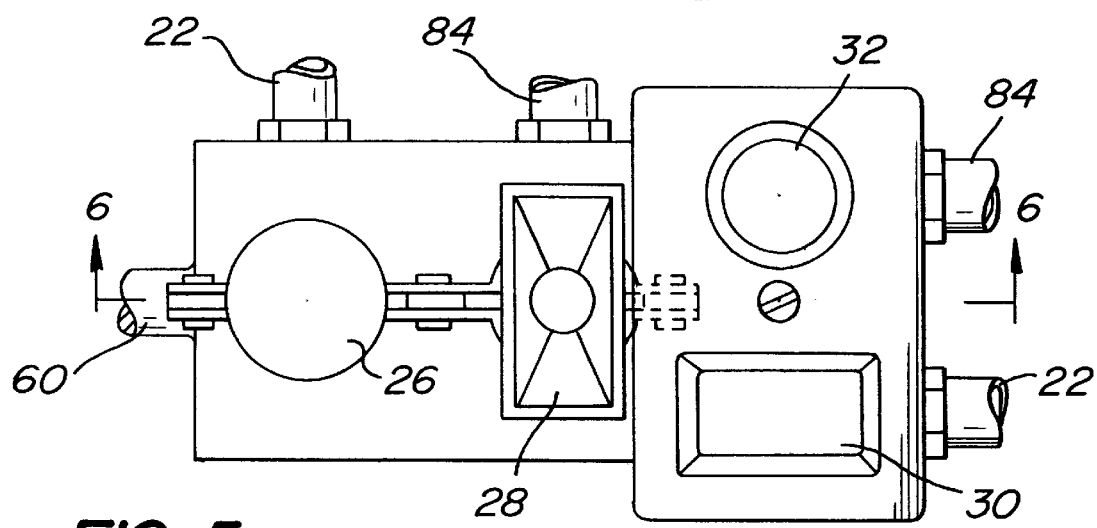
FIG. 5 is an enlarged top elevational view of the telescopic housing, as indicated by line 5—5 of FIG. 3.
Figure 6:
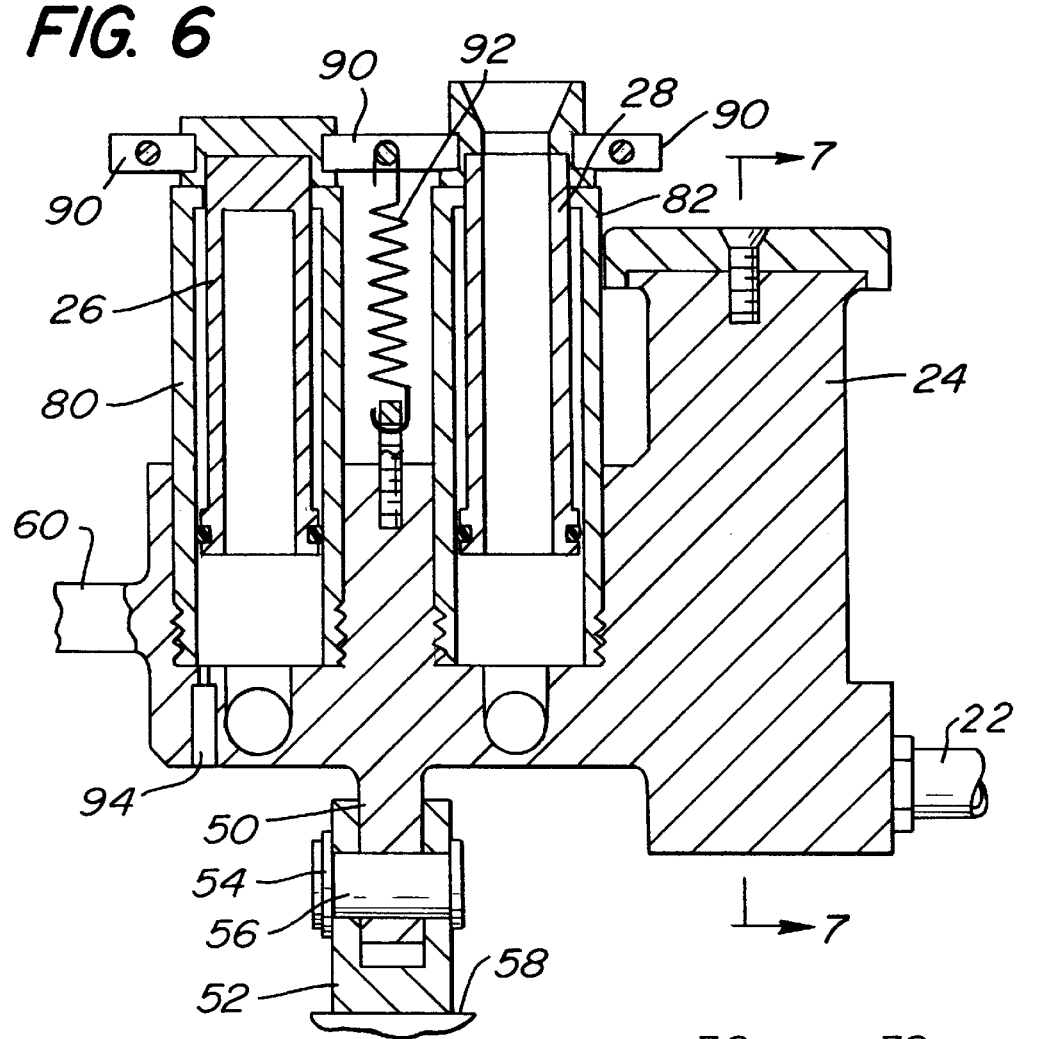
FIG. 6 is an enlarged cross-sectional view of the telescopic housing of FIG. 5, taken along line 6—6 of FIG. 5.
Figure 7:
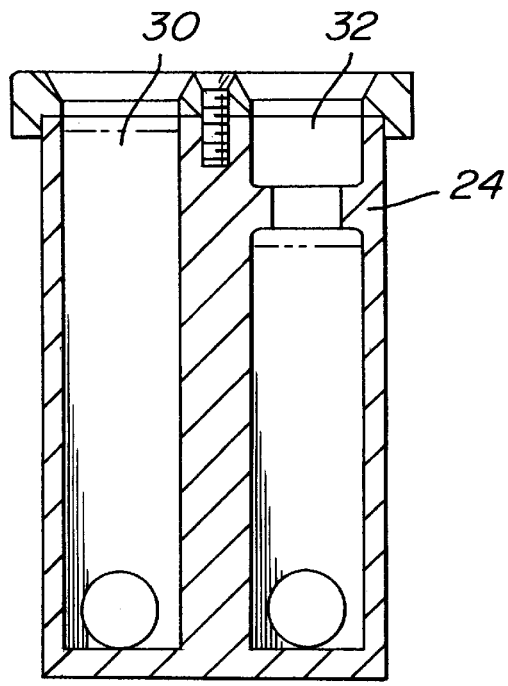
FIG. 7 is a cross-sectional view of the telescopic housing of FIG. 5, taken along line 7—7 of FIG. 6.

As best shown in FIG. 5, the pin assembly 140 comprises a piston 144, a spring 146, a guide plug 148, an o-ring 150, and a pin 124. When compressed air enters the cylindrically-shaped cavity 138, the cylindrically-shaped piston 144 is forced towards the outside surface of the traction wheel 114. The pin 124 is an integral part of the piston 144 and extends from the top surface of the piston. As the piston 144 is pushed upward toward the external surface of the traction wheel 114 by the force of compressed air, the pin 124 is simultaneously pushed outward through a bore in the guide plug 148. The guide plug 148 is cylindrically-shaped and has a top section 149 and a bottom section 151. The top section 149 of the guide plug 148 has a circumference equivalent to the circumference of the piston 144. The bottom section 151 of the guide plug 148 has a smaller circumference than the top section 149. The top 149 and bottom 151 sections of the guide plug 148 and the bore share a common centerline. The upward movement of the piston is opposed by the spring 146 acting against the guide plug 148. The spring 146 is located between the top surface of the piston and the guide plug 148 such that the spring 146 envelops the bottom section of the guide plug, occupying the space between the cavity 138 and the guide plug 148. In a preferred embodiment, the pin 124 extends through the guide plug 148 and the outer surface of the wheel 100 about 0.1875 inches.

To retract the pins, the operator throws the air switch which releases the air pressure. The spring 146 forces the piston 144 and the pin 120 the return to the retracted position. The piston 144 contains an o-ring 150 which enables a seal to be formed between the piston 144 and the cavity 138 wall, thus allowing air pressure to be maintained.

Although the present invention has been described in detail in connection with the above embodiments, it is to be understood that such detail is solely for that purpose and that variations can be made by those skilled in the art without departing from the spirit of the invention except as it may be limited by the following claims.

What is claimed is:

1. A robotic sampling device for collecting samples from process streams in piping networks, comprising:

a. a front end and a back end, and a propulsion module and a sample collecting module intermediate the front and back ends;

b. a maneuverable, telescoping sample collector supported by said sample collecting module, comprising a telescopic sampling housing; a telescoping sampling arm; means for extending the sample collecting arm; means for rotating the sampling collecting arm through a 180° arc relative to the axis of the pipe; means for retracting the sample collecting arm; a pump providing suction; a sampling line connecting the sample collecting arm to the pump; means for identifying and storing a sample collected by the sample collecting arm; and means for flushing the sample collector;

c. the propulsion module containing means for supporting movement and facilitating movement of the robotic sampling device;

d. means for increasing traction for the propulsion module with respect to a supporting surface exterior to the robotic sampling device connected to the propulsion module;

e. at least one light source on said front end;

f. viewer connected to the robotic sampling device for providing information for navigation and sample collection; and g. means for remotely controlling the robotic sampling device.

2. The robotic sampling device as in claim 1, wherein the means for supporting movement and facilitating movement comprises wheels.

3. A robotic sampling device as in claim 2, wherein the propulsion module comprises:

a. a motor, and b. means for coupling the motor to the wheels.

4. A robotic sampling device as in claim 3, wherein the means for coupling the motor to the wheels comprises:

a. at least one drive shaft attached to said wheels;

b. a chain connecting the motor to a sprocket on each drive shaft.

5. A robotic sampling device as in claim 1, wherein the means for extending the telescopic sampling arm comprise a piston operatively connected to the telescoping sampling arm.

6. A robotic sampling device as in claim 3, wherein the operative connection is a clamp connecting the piston to the telescopic sampling arm.

7. A robotic sampling device as in claim 6, wherein the means for extending the telescopic sampling arm further comprises a supply of compressed air, wherein the compressed air forces the movement of the piston.

8. A robotic sampling device as in claim 1, wherein the means for retracting the telescopic arm comprises a spring for applying a retracting force.

9. A robotic sampling device as in claim 8, wherein the spring attaches to a clamp, the clamp attached to the telescopic arm, and the spring further attached to the telescopic sampling housing where the spring pulls the telescopic sampling arm.

10. A robotic sampling device as in claim 1, wherein the means for flushing the sample collection system comprise:

a. a supply of distilled water;

b. a solenoid valve; and c. a pump, wherein the pump flushes distilled water, directed by the solenoid valve, through the sampling line and the telescopic sampling arm.

11. A robotic sampling device as in claim 1, wherein the means for rotating the telescopic sampling arm through a 180° arc relative to the axis of the pipe comprises a means for tilting the telescopic sampling housing.

12. A robotic sampling device as in claim 11, wherein the means for tilting the telescopic sampling housing comprises:

a. a motor;

b. a drive shaft attached to the motor;

c. a rotating assembly connecting the drive shaft to the telescopic sampling housing; and d. a telescopic sampling housing mounting assembly.

13. A robotic sampling device as in claim 12, wherein the rotating assembly further comprises:

a. a mounting bracket connected to the drive shaft;

b. a coupling attached to the mounting bracket;

c. a connecting rod connected to the coupling; and d. a shaft on the telescopic sampling housing secured to the connecting rod.

14. A robotic sampling device as in claim 12, wherein the telescopic sampling housing assembly comprises:

a. a mounting shaft on the telescopic sampling housing;

b. the mounting shaft connected to a mounting bracket; and c. the mounting bracket secured to a platform.

15. A robotic sampling device as in claim 1, wherein the propulsion module comprises:

a. a motor, and b. means for coupling the motor to the means for supporting and facilitating movement.

16. A robotic sampling device as in claim 15, wherein the means for coupling the motor to the means for supporting and facilitating movement comprises:

a. at least one drive shaft;

b. a chain connecting the motor to a sprocket on each drive shaft; and c. means for supporting and facilitating movement attached to opposite ends of each drive shaft.

17. A robotic sampling device as in claim 1, wherein the means for increasing traction for the propulsion module comprises a plurality of extendable pins.

18. A robotic sampling device as in claim 17, wherein the extendable pins are located within pin assemblies positioned within the means for supporting and facilitating movement of the propulsion module.

19. A robotic sampling device as in claim 18, wherein the means for supporting and facilitating movement are wheels.

20. A robotic sampling device as in claim 18, wherein the pins may be extended beyond the outer surface of the means for supporting and facilitating movement under the force of compressed air and retracted in the absence of the force of compressed air.

21. A robotic sampling device as in claim 20, wherein the means for supporting and facilitating movement are wheels.

22. A robotic sampling device as in claim 21, wherein the wheels further comprise an inner diameter and outer diameter wherein the inner diameter of the wheel is larger than the outer diameter of the wheel.

23. A robotic sampling device as in claim 18, wherein the pin assemblies further comprise:

a. a cylindrical piston containing an integral, cylindrical pin projecting from a top surface of the piston;

b. a cylindrical guide plug having a top section and a bottom section wherein the top section has a circumference equivalent to the circumference of the piston and the bottom section having a smaller circumference;

c. the guide plug containing a central bore having a diameter chosen to accommodate the pin therethrough;

d. the pin assembly located in a cylindrical cavity in the wheel having a diameter accommodating the guide plug and piston;

e. a spring located between the top surface of the piston and the guide plug, wherein the spring envelopes the bottom section of the guide plug, occupying the space between the cavity and the guide plug; and f. the piston adapted to receive and o-ring to form a seal between the cavity and the piston.

24. A robotic sampling device as in claim 1, wherein said at least one light source is located in the proximity of the telescoping sampling collection system and further comprising at least one light source located on the front end of the robotic sampling device.

25. A robotic sampling device as in claim 1, wherein the viewer for providing information comprises at least one video camera.

26. A robotic sampling device as in claim 25, wherein said at least one video camera is on the sample collector and further comprising at least one camera located on the front end of the robotic sampling device.

27. A robotic sampling device as in claim 1, wherein the means for remotely controlling the robotic sampling device comprised of an umbilical cord connected to the removable telescoping sample collection system and the mobilizing drive module to a central command console, the umbilical cord containing a plurality of cords having a smaller diameter than the umbilical cord wherein at least one cord is adapted to deliver compressed air and at least one cord is adapted to deliver electrical power.

28. A remote-controlled sampling module for collecting samples from process streams in piping networks, comprising:

a. a housing;

b. a maneuverable, extendable, retractable telescoping sample collecting arm supported by the housing and rotatable through a 180° arc relative to the axis of the pipe;

c. a remotely-controlled pump within the housing and connected to the sample collecting arm via a sampling line, the pump alternately providing suction for sample collection and pressure for sampling line flushing;

d. a remotely-controlled switch valve positioned within a solenoid valve in the sampling line to regulate fluid flow therein;

e. sample collection containers located inside the housing to receive sampled analyte from the sample collecting arm;

f. means within the housing for labeling the sample collection containers; and g. means for flushing the sampling line with distilled water, said means connected to the pump and a source of distilled water external to and separate from the sampling module.

\* \* \* \* \*